United States Patent [19]

Ayers et al.

[11] Patent Number: 5,574,171
[45] Date of Patent: *Nov. 12, 1996

[54] ENANTIOSELECTIVE HYDROFORMYLATION

[75] Inventors: Timothy A. Ayers; Thaliyil V. Rajanbabu, both of Wilmington, Del.

[73] Assignee: E. I. Du Pont de Nemours and Company, Wilmington, Del.

[*] Notice: The term of this patent shall not extend beyond the expiration date of Pat. No. 5,481,006.

[21] Appl. No.: 427,328

[22] Filed: Apr. 24, 1995

Related U.S. Application Data

[62] Division of Ser. No. 116,235, Sep. 2, 1993, Pat. No. 5,475,146.

[51] Int. Cl.$^6$ .............. C07F 15/00; B01J 31/00
[52] U.S. Cl. .......... 549/206; 549/220; 549/221; 549/222; 556/20; 556/136; 556/138; 502/166
[58] Field of Search .......... 556/20, 136, 138; 549/206, 220, 221, 222; 502/166

[56] References Cited

U.S. PATENT DOCUMENTS

| | | | |
|---|---|---|---|
| 4,268,688 | 5/1981 | Tinker et al. | 560/177 |
| 4,554,262 | 11/1985 | Dessau | 502/62 |
| 4,654,176 | 3/1987 | Dang et al. | 260/505 R |
| 4,666,874 | 5/1987 | Dessau | 502/62 |
| 5,099,077 | 3/1992 | Petit et al. | 568/814 |

FOREIGN PATENT DOCUMENTS

| | | |
|---|---|---|
| 1027141 | 2/1978 | Canada. |
| 0443923 | 8/1991 | European Pat. Off.. |
| 0498507 | 8/1992 | European Pat. Off.. |
| 0512416 | 11/1992 | European Pat. Off.. |
| 2208872 | 8/1974 | France. |
| 275623 | 1/1990 | Germany. |
| 275671 | 1/1990 | Germany. |
| 280473 | 7/1990 | Germany. |
| 280527 | 7/1990 | Germany. |
| 280474 | 7/1990 | Germany. |
| 280529 | 7/1990 | Germany. |
| 280528 | 7/1990 | Germany. |
| 1389802 | 4/1975 | United Kingdom. |
| WO93/03839 | 3/1993 | WIPO. |

OTHER PUBLICATIONS

Botteghi, C. et al, *Chirality*, 3, 355–369 (1991).
Stille, J. K. et al, *Organometallics*, 10, 1183–1189 (1991).
Parrinello, G. et al, *J. Am. Chem. Soc.*, 109, 7122–7127 (1987).
Consiglio, G. et al, *Organometallics*, 10, 2046–2051 (1991).
Mortreux, A. et al, "Preparation of Chiral Ligands from Aminoacids, Application to Catalytic Asymmetric Synthesis: A Review", *Bulletin de la Societe Chimique de France*, 4, 631–639 (1987).
Toth, I. et al, *Organometallics*, 12, 848–852 (1993).
Jackson, W. R. et al, *Aust. J. Chem.*, 35, 2069–2075 (1982).
Brown, J. M. et al, *Tetrahedron*, 42(18), 5105–5109 (1986).
Ceriotti, A. et al, *J. of Molecular Catalysis*, 24, 309–321 (1984).
Sakai, N. et al, *Tetrahedron: Asymmetry*, 3(5), 583–586 (1992).
Zhou, J. Q. et al, *J. Chem. Soc., Chem. Commun.*, pp. 233–234 (1991).
Amer, I. et al, *J. Am. Chem. Soc.*, 112, 3674–3676 (1990).
Neibecker, D. et al, *J. Org. Chem.*, 54, 5208–5210 (1989).
Wink, D. J. et al, *Inorg. Chem.*, 29, 5006–5008 (1990).
Selke, R. et al, *J. of Molecular Catalysis*, 56, 315–328 (1989).
Selke, R., *J. of Molecular Catalysis*, 37, 227–234 (1986).
Rajanbabu, T. V., *J. Am. Chem. Soc.*, 114, 6265–6266 (1992).
Selke, R., *React. Kinet. Catal. Lett.*, 10(2), 135–138 (1979).
Selke, R. et al, *J. of Molecular Catalysis*, 37, 213–225 (1986).
Selke, R., *J. of Organometallic Chemistry*, 370, 249–256 (1989).
Jackson, R., *J. of Organometallic Chemistry*, 159, C29–C31 (1978).
Cullen, W. R. et al, *Tetrahedron Letters*, 19, 1635–1636 (1978).
Selke, R., *J. f. prakt, Chemie*, 329(4), 717–724 (1987).
Selke, R. et al, *Tetrahedron: Asymmetry*, 4(3), 369–382 (1993).
Johnson, T. H. et al, *J. Org. Chem.*, 44(11), 1878–1879 (1979).
Johnson, T. H., *J. Org. Chem.*, 45, 62–65 (1980).
Johnson, T. H. et al, *J. of Molecular Catalysis*, 9, 307–311 (1980).
Habus, I. et al, *J. of Molecular Catalysis*, 42, 173–181 (1987).
Capka, M. et al, *React. Kinet. Catal. Lett.*, 10(3), 225–228 (1979).
Selke, R., *J. of Organometallic Chemistry*, 370, 241–248 (1989).
Brunner, H. et al, *J. Chem. Research*, (S), 76, (1980).
Bourson, J., *J. of Organometallic Chemistry*, 229, 77–84 (1982).
Sunjic, V. et al, *Gazzetta Chimica Italiana*, 119, 229–233 (1989).
Yamashita, M. et al, *Bull. Chem. Soc. Japan*, 62(3), 942–944 (1989).
Nakamura, Y. et al, *Chem. Letters*, pp. 7–10 (1980).
Yamada, M. et al, *Carbohydrate Research*, 95, C9–C12 (1981).
Yamashita, M. et al, *Bull. Chem. Soc. Japan*, 55, 2917–2921 (1982).

(List continued on next page.)

*Primary Examiner*—Porfirio Nazario-Gonzales

[57] ABSTRACT

Enantioselective hydroformylation of vinyl compounds using a catalyst composition of a chiral carbohydrate phosphorous ligand with a Rh, Pt, Co or Ir metal, to produce chiral 2-substituted propanals, wherein the phosphorous of the ligand is substituted with electron withdrawing groups.

6 Claims, No Drawings

OTHER PUBLICATIONS

Saito, S. et al, *Chem. Pharm. Bull.,* 33(12), 5284–5293 (1985).

Yamashita, M. et al, *Bull. Chem. Soc. Japan,* 59, 175–178 (1986).

Cesarotti, E. et al, *Gazzetta Chimica Italiana,* 117, 129–133 (1987).

Habus, I., Croatica Chemica Acta, 61(4), 857–866 (1988).

Hatat, C. et al, *Tetrahedron Letters,* 29(30), 3675–3678 (1988).

Dobler, C. et al, *J. of Organometallic Chemistryi,* 344, 89–92 (1988).

Krause, H. W. et al, *New J. Chem.,* 13, 615–620 (1989).

Sunjic, F. et al, *J. of Organometallic Chemistry,* 370, 295–304 (1989).

Hatat, C. et al, *Tetrahedron Letters,* 31(29), 4139–4142 (1990).

Taudien, S. et al, *Tetrahedron: Asymmetry,* 4(1), 73–84 (1993).

ENANTIOSELECTIVE HYDROFORMYLATION

CROSS-REFERENCE TO RELATED APPLICATION

This application is a division of U.S. application Ser. No. 08/116,235 filed Sep. 2, 1993, now U.S. Pat. No. 5,475,146.

FIELD OF THE INVENTION

The present invention relates to enantioselective hydroformylation of vinyl compounds R—CH=CH$_2$ to produce chiral nonracemic 2-substituted 1-propanals of the formula R—CH(CHO)CH$_3$; wherein a catalyst composition of the reaction comprises Rh, Pt, Co or Ir, and a chiral, nonracemic carbohydrate phosphorous ligand wherein the phosphorus is substituted with electron withdrawing groups.

BACKGROUND OF THE INVENTION

It is known in the art that optically active diphosphinites derived from carbohydrates can be used as ligands for the metals Rh and Pt in the asymmetric hydroformylation of vinyl arenes. The major problem that has plagued the well-known Pt-catalyzed hydroformylations, however, is the unfavorable branched to linear ratios which reduce overall selectivity. The Rh-catalyzed reactions generally give good branched to linear ratios but enantioselectivity is poor. A series of metal/ligand combinations which overcome these limitations is the subject of this application.

Ojima, I. and Hirai, K., *"Asymmetric Hydrosilylation and Hydrocarbonylation"* in Asymmetric Synthesis; Morrison, J. D., Ed.; Academic Press, Orlando, Fla., 1985; pp 103–146 and Jackson, W. R. and Lovel, C. G., *Aust. J. Chem.*, 35, 2069–75 (1982) describe low asymmetric induction in the hydroformylation of vinyl acetate in the presence of a phosphinite derived from tartaric acid.

German patents DD280,473, DD275,623 and DD275,671 and references Selke et al., *J. Mol. Cat.*, 37, 213–225 (1986) and Selke, *J. Organometal. Chem.*, 370, 249–256 (1989) disclose related rhodium carbohydrate catalysts mainly for enantioselective hydrogenation reactions, but no teaching is provided which demonstrates or enables effective enantioselective hydroformylation, and the importance of electronic effects of these ligands is not suggested.

Ligands similar to those used in the present invention are disclosed in RajanBabu, T. V. and Casalnuovo, A. L., *J. Am. Chem. Soc.*, 114, 6265–6266 (1992) and U.S. Pat. No. 5,175,335, for use in other catalyst compositions for asymmetric hydrocyanation.

High enatioselectivities are most often explained on the basis of steric arguments, see for example, Brown, J. M., *Chem. Soc. Rev.*, 25 (1993), and references cited therein. For a recent example of the application of classical and widely used steric approach to design of enantioselective catalysts see: Trost, B. M. et al. *J. Am. Chem. Soc.* 114, 9327 (1992) and references cited therein. Recently, electronic effects are described as being effective in enhancing enantioselectivity in manganese-catalyzed oxidation, Jacobsen, E. N. et al., *J. Am. Chem. Soc.* 113, 6703, (1991), and in nickel-catalyzed hydrocyanations, RajanBabu, T. V. and Casalnuovo, A. L., *J. Am. Chem. Soc.*, 114, 6265–6266 (1992). No teaching of electronic effects in the enantioselective hydroformylation reaction have been described.

SUMMARY OF THE INVENTION

The present invention provides a process for enantioselective hydroformylation comprising: reacting a vinyl compound of formula I $$R—CH=CH_2 \qquad \qquad I$$

with a source of CO and H$_2$, in the presence of a catalyst composition comprising one or more metals selected from the group consisting of Co, Rh, Ir, and Pt, and a chiral, nonracemic ligand of formula II $$(R^1)_2—P—O—R_2—O—P—(R^1)_2 \qquad \qquad II$$

to produce a nonracemic hydroformylated product of formula III

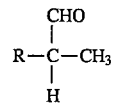

$$\qquad \qquad III$$

wherein:

R is a C$_1$ to C$_{20}$ carboalkoxy, a C$_1$ to C$_{40}$ hydrocarbyl, or a C$_1$ to C$_{40}$ heterocyclic radical; each optionally substituted with one or more halo, alkoxy, carboalkoxy, hydroxy, amido or keto groups;

each R$^1$ is an electron-withdrawing group comprising an aromatic hydrocarbyl substituted with one or more halo, halogen-substituted alkyl groups, cyano, alkylsulfonyl, carboalkoxy, quaternary ammonium, nitro, amido or keto groups; or a heteroaromatic optionally substituted with one or more halo, halogen-substituted alkyl groups, cyano, alkyl sulfonyl, carboalkoxy, quaternary ammonium, nitro, amido or keto groups;

R$^2$ is a C$_4$ to C$_{40}$ dideoxy carbohydrate optionally substituted with one or more hydrocarbyl, halo, alkoxy, carboalkoxy, hydroxy, amido or keto groups.

The present invention also provides a novel catalyst composition comprising one or more metals selected from the group consisting of Co, Rh, Ir and Pt, and one or more chiral nonracemic ligands of formula II $$(R^1)_2—P—O—R^2—O—P—(R^1)_2 \qquad \qquad II$$

wherein:

each R$^1$ is an electron-withdrawing group comprising an aromatic hydrocarbyl or heteroaromatic, optionally substituted with one or more halo, halogen-substituted alkyl groups, cyano, alkyl sulfonyl, carboalkoxy, quaternary ammonium, nitro, amido or keto groups; and R$^2$ is a C$_4$ to C$_{40}$ dideoxy carbohydrate; optionally substituted with one or more hydrocarbyl, halo, alkoxy, carboalkoxy, hydroxy, amido or keto groups.

DETAILED DESCRIPTION OF THE INVENTION

The process of the instant invention, whereby enantioselective hydroformylation is accomplished by reacting a vinyl compound of the formula R—CH=CH$_2$ with hydrogen and carbon monoxide in the presence of a chiral, nonracemic, metal (Rh, Pt, Ir or Co) hydroformylation catalyst, is useful, for example, to produce 2-substituted-1-propanals. For example, vinyl arenes are precursors to nonsteroidal, antiinflammatory drugs such as ibuprofen and naproxen. The novel catalyst compositions of the instant invention, comprising a metal and chiral, nonracemic diphosphinite ligand derived from a carbohydrate diol, are useful for accomplishing the above-described enantioselective hydroformylation reactions.

The enantioselective hydroformylation reaction of the invention is performed by reacting a vinyl compound of the formula R—CH=CH$_2$ with hydrogen and carbon monoxide at pressures of about 100–2400 psi (1 psi=6.9 kPa) in the presence of a chiral, nonracemic, metal (Rh, Pt, Ir or Co) hydroformylation catalyst. These reactions produce chiral, nonracemic, 2-substituted-1-propanals of the formula R—CH(CHO)CH$_3$, herein called branched aldehydes. Undesired products, 3-substituted-1-propanals are also generated, herein called linear aldehydes. The selectivity of this reaction will be reported herein by the ratio of branched aldehyde (b) to the linear aldehyde (1).

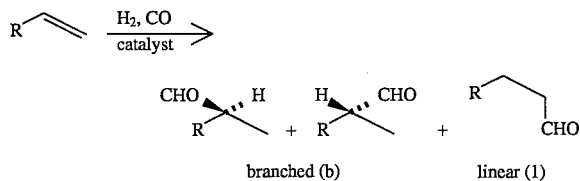

By the term "carbohydrate", Applicants mean the class of organic compounds comprising the general formula (CH$_2$O)$_n$, wherein n is equal to or greater than four. The carbohydrate-derived ligands of the invention are derived from C$_4$ to C$_{40}$ carbohydrates including monosaccharides, disaccharides and oligosaccharides.

By the term "heterocycle", Applicants mean a cyclic carbon compound containing at least one oxygen, nitrogen or sulfur atom in the ring.

By the term "hydrocarbyl", Applicants include all alkyl, aryl, aralkyl or alkylaryl carbon substituents, either straight-chained, cyclic, or branched, accordingly substituted with hydrogen. The term "hydrocarbyl" as used herein includes both aromatic and nonaromatic hydrocarbyls.

By the term electron-withdrawing group, Applicants include those groups that have σ-values (any, σ-values such as σ$_p$, σ$_m$, σ$_I$, σ$_R$, etc.) greater than or equal to 0.1 (as defined by the Hammett equation, see for example March, J. Advanced Organic Chemistry, Reactions, Mechanisms, and Structure, 4th ed.; 1992, Wiley: New York, pp 278–286).

In describing a carbohydrate group of the formula O—R$^2$—O, as it appears within the ligand of the present disclosure, the group R$^2$ is named by using the prefix "dideoxy" with the name of the parent diol of the formula HO—R$^2$—OH. For example, the name 2,3-dideoxyglucose refers to the group:

and accordingly, the corresponding carbohydrate group O—R$^2$—O is:

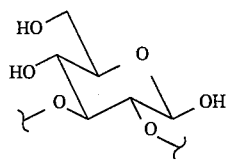

The suffix -ose- when used in combination with carbohydrate root names, shall include those compounds wherein the OH groups are protected as ethers or esters. By this definition, for example, the glucopyranoside structure shown below is termed "a glucose"

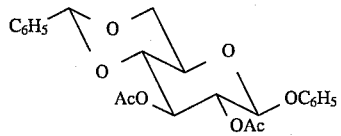

wherein Ac is an acetyl.

By the term "chiral", Applicants mean "existing as a pair of enantiomers". These enantiomers, where the chiral centers are designated the R and S isomers, are nonsuperimposable mirror images of one another. A chiral material may either contain an equal amount of the R and S isomers in which case it is called "racemic" or it may contain inequivalent amounts of R and S isomer in which case it is called "optically active", or "nonracemic".

By the term "enantiomeric excess" ("ee"), Applicants mean the absolute-difference between the percent of R enantiomer and the percent of S enantiomer of an optically active compound. For example, a compound which contains 75% S isomer and 25% R isomer will have an enantiomeric excess of 50%.

By the term "enantioselective" Applicants mean the ability to produce a product in an optically active form.

The substrates of the invention are described by the formula R—CH=CH$_2$, where R may be any C$_1$ to C$_{20}$ carboalkoxy, C$_1$ to C$_{40}$ hydrocarbyl or C$_1$ to C$_{40}$ heterocyclic radical; each of which may be substituted with one or more halo, alkoxy, carboalkoxy, hydroxy, amido or keto groups. Examples of R include, but are not limited to, phenyl, substituted phenyl, polyaromatic (e.g., naphthyl, anthryl), substituted polyaromatic, acetoxy, alkyl and substituted alkyl. Representative examples of substrates used in the invention include, but are not limited to, 2-vinylnaphthalene, 6-methoxy-2 -vinylnaphthalene, vinyl acetate, 4-isobutylstyrene, 4-methylstyrene and styrene.

The vinyl substrates of the invention may be made by methods which are well-known in the art e.g., Organometallics, 10, 1183–1189 (1991), which is hereby incorporated by reference. Many substrates are also available commercially.

The chiral, nonracemic carbohydrate diphosphinite ligands of the invention are defined as (R$^1$)$_2$—P—O—R$^2$—O—P—(R$^1$)$_2$, wherein R$^1$ may be an aromatic hydrocarbyl substituted with one or more halo, halogen-substituted alkyl groups, cyano, alkyl sulfonyl, carboalkoxy, quaternary ammonium, nitro, amido or keto groups; or a heteroaromatic optionally substituted with one or more halo, halogen-substituted alkyl groups, cyano, alkyl sulfonyl, carboalkoxy, quaternary ammonium, nitro, amido or keto groups. These ligands are unique in this art in that the R$^1$ group of the ligand is an electron-withdrawing group as defined herein. Applicants have discovered that electron-withdrawing groups generally lead to high selectivity in the hydroformylation method of this invention.

For all embodiments of the Applicants' invention, the chiral, nonracemic, metal hydroformylation catalyst composition comprises a chiral, nonracemic, carbohydrate diphosphinite ligand and a source of one or more of the metals Rh, Pt, Co and It. Suitable sources of the rhodium, platinum, cobalt, and iridium include, but are not limited to, the metal halides, olefin complexes, acetoacetates, and carbonyls. Metal compounds that contain ligands which can be displaced by the chiral carbohydrate phosphorus ligand are a preferred source of the metal. In the case, for example, of rhodium (I) intermediates, $(COD)_2RhX$ species (COD is 1,5-cyclooctadiene) are the precursors of choice, with the counterion X being tetrafluoroborate ($BF_4$), antimony hexafluoride ($SbF_6$), or trifluoromethanesulfonate (OTf); although other counterions such as tetraphenylborate ($BPh_4$) and perchlorate ($ClO_4$) would also be suitable. Chiral iridium compounds can be prepared from $[(COD)IrCl]_2$. Platinum compounds can be synthesized from dichloro-bis-(benzo-nitrile)platinum (II). Cobalt compounds can be prepared from cobalt carbonyl. Rhodium is the preferred metal.

The catalyst composition also employs a ligand comprising a chiral, nonracemic diphosphinite of the formula $(R^1)_2-P-O-R^2-O-P-(R^1)_2$, wherein the $R^2$ is a $C_4$ to $C_{40}$ dideoxycarbohydrate, optionally substituted with one or more hydrocarbyl, halo, alkoxy, carboalkoxy, hydroxy, amido or keto groups; and such that the fragment of the ligand defined by the structure $PO-R^2-OP$ is chiral. By this definition Applicants intend that the chirality of the diphosphinite ligand arises from the chirality of the parent carbohydrate diol $HO-R^2-OH$.

Specifically, the process is carried out by employing chiral, nonracemic, O-substituted carbohydrate phosphorus ligands; including particularly pyranose, furanose, disaccharide and oligosaccharide organophosphorus ligands. Examples are represented by the formulas IV, V, VI and VII,

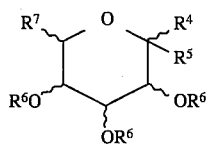

IV

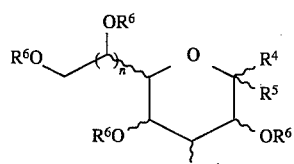

V

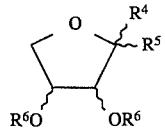

VI

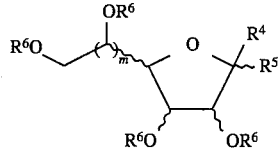

VII wherein:

n=0–2;

m=0–3;

$R^4$ groups are independently H, hydroxy, $C_1$ to $C_{20}$ hydrocarbyl, alkoxy, aryloxy, O-substituted pyranose or O-substituted furanose;

$R^5$ groups are independently H, hydroxymethyl ($CH_2OH$), alkoxymethyl, aryloxymethyl, or $CH_2OP(X)_2$ where X is aryl, alkoxy, or aryloxy;

$R^6$ groups are independently H, $C_1$ to $C_{20}$ hydrocarbyl, acyl, or $P(X)_2$ where X is aryl, alkoxy, or aryloxy;

$R^7$ is H or $CH_3$;

and the sum total of $P(X)_2$ groups present in the O-substituted pyranose, furanose, dissacharide or oligosaccharide organophosphorus ligand is equal to 2.

Applicants also specifically include within the carbohydrate ligand compositions of the invention those carbohydrates containing protective groups. By the term "protective group", Applicants include groups such as ethers and esters which function to provide chiral recognition of the sugar molecule, and further are commonly employed to protect the sugar molecule from nonselective reactions. Applicants further intend to particularly include disaccharides formed by joining two of the structures shown in formulas IV–VII through an oxygen atom at the anomeric position of the furanose or pyranose ring. Two examples of such dissacharides are shown below, wherein Ph is phenyl and Ac is acetyl.

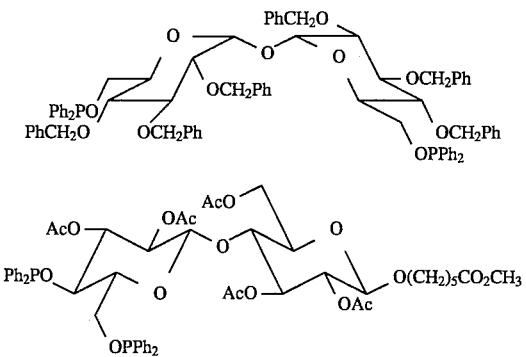

Most preferably, the chiral, nonracemic, organophosphorus ligand is a chiral, nonracemic, O-substituted glucopyranose organophosphorus ligand of the formula VIII,

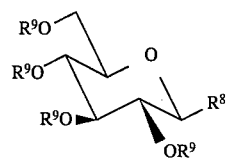

VIII wherein:

$R^8$ is H, hydroxy, $C_1$ to $C_{20}$ hydrocarbyl, alkoxy, or aryloxy;

$R^9$ is independently selected from H, $C_1$ to $C_{20}$ hydrocarbyl, acyl or $P(X)_2$, where X is aryl, alkoxy, aryloxy;

and the sum total of $P(X)_2$ groups present in the O-substituted glucopyranose organophosphorus ligand is equal to 2.

Chiral, nonracemic O-substituted carbohydrate derived diolphosphorus ligands can be prepared according to techniques well-known in the art. [*J. Organomet. Chem.*, 159, C29 (1978); *Tetrahedron Lett.*, 1635 (1978); *J. Org. Chem.*, 45, 62 (1980); *Bull. Chem. Soc. Jpn.*, 59, 175 (1986); *J. Mol. Catal.*, 37, 213 (1986); *J. Prakt. Chem.*, 329 (4), 717 (1987)]. In general, diol derivatives containing unprotected hydroxyl groups are treated with a $P(R)_2Cl$ (wherein R may generally be an alkyl, aryl, alkoxy, or aryloxy) reagent, in the presence of a base, such as pyridine or triethylamine, to produce the desired phosphinite or phosphite. Some $P(R)_2Cl$ reagents are commercially available, such as PPh$_2$Cl (Ph= phenyl). Other P(R)$_2$Cl reagents, where R=aryl or alkyl, can be prepared by two methods. Method A involves the reaction of (amino)dichlorophosphines such as Et$_2$NPCl$_2$ with RMgBr followed by reaction with HCl [*J. Am. Chem. Soc.* 2148, 82, (1960)]; *J. Am. Chem. Soc.* 80, 1107 (1958). Alternatively, treatment of readily available dialkyl phosphites, such as dibutyl phosphite, HP(O)(OBu)$_2$, with RMgBr followed by reaction with PCl$_3$ provides P(R)$_2$Cl derivatives. [*J. Am. Chem. Soc.* 73, 4101 (1951); *J. Am. Chem. Soc.*, 74, 5418 (1952)]; *J. Org. Chem.*, 31, 1206 (1966). P(R)$_2$Cl reagents, where R=alkoxy or aryloxy, can be prepared in two steps by treatment of P(NEt$_2$)$_3$ with ROH to generate P(OR)$_2$(NEt$_2$), followed by treatment with CH$_3$COCl to generate P(OR)$_2$Cl. Illustrative preparations are provided below.

For all embodiments of the invention the chiral, nonracemic metal hydroformylation catalyst may be prepared by mixing the metal source and the chiral, nonracemic, organophosphorus ligand, preferably in a suitable organic solvent under an inert atmosphere such as N$_2$ or Ar in a temperature range from 0° C. to 120° C., preferably in a temperature range from 0° C. to 80° C. The metal compound may be used in this solution or the metal compound can be obtained in the pure form upon removal of the solvent.

The molar ratio of chiral, nonracemic, organophosphorus ligand to the metal may vary between 1:1 to 10:1, preferably between 1:1 to 1.2:1.

The molar ratio of metal complex to vinyl compound may vary between 0.0001:1 to 1:1, preferably between 0.0025:1 to 0.05:1.

The vinyl compound starting material, which is represented by the formula R—CH=CH$_2$ may be dissolved in any organic solvent compatible with the reagents employed, preferably a nonpolar solvent (nonpolar solvents generally provide higher ee's) such as, but not limited to, benzene, hexane, or triethylsilane. In the case of a liquid substrate, the substrate itself can serve as the solvent.

The H$_2$ and CO can be provided by contacting the reaction mixture with the gases and can be provided in mixtures of H$_2$ to CO ranging from 10:1 to 1:10.

A preferred 1:1 mixture of H$_2$ and CO can be conveniently prepared or purchased commercially. The pressures of H$_2$ and CO under which the hydroformylation reactions can be conducted range generally from 100–2400 psi (1 psi=6.9 kPa), with 500–1000 psi being the preferred pressure. The pressure employed is not critical; for example, in the case of the hydroformylation of 2-vinylnapthalene in hexane at room temperature using catalyst 1, the following ee's were obtained with the pressure of H$_2$ and CO (1:1) indicated: 49% (500 psi), 51% (1600 psi), and 31% (2400 psi).

The hydroformylation reaction is preferably carried out over a temperature range from 20° to 80° C., most preferably 25° to 30° C. Applicants note that the observed overall selectivity (ee's and branched to linear ratios) generally decreases as the temperature is increased. For example, the hydroformylation of 2-vinylnapthalene in benzene at 1600 psi provides an ee of 10% when the reaction is performed at room temperature and 1% at 70° C. The branched to linear ratio in this case falls from 21:1 (room temperature) to 12:1 (70° C.). In addition, the ee of the hydroformylation of 2-vinylnapthalene decreases from 12% to 11% when the reaction is conducted in THF at room temperature versus 70° C. The branched to linear ratio also decreases in the latter example from 40:1 (room temperature) to 10:1 (70° C.).

The enantioselective hydroformylation reactions are generally complete within 18–48 hours. In the case of platinum catalysts, the presence of a Lewis acid such as tin (II) chloride is typically preferred.

To demonstrate a preferred mode of the invention which produces a particularly useful product, preparation of optically active (S)-(−)-2-(6-methoxy-2-naphthalene)propanal, can be achieved. The catalyst composition comprises a cationic rhodium (I) compound and the ligand of formula II wherein each R$^1$ is the aryl group 3,5-bis(trifluoromethyl)phenyl and R$^2$ is the O-substituted β-D-glucopyranose derivative of the formula IX, the starting vinyl compound is 6-methoxy-2-vinylnaphthalene, and the preferred source of the rhodium(I) species is (COD)$_2$RhBF$_4$.

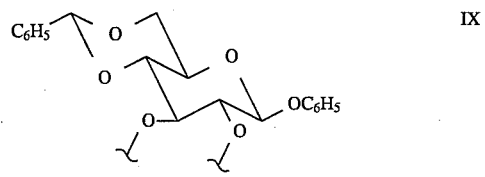

IX

For the preparation of optically active (S)-(−)-2-(6-methoxy-2-naphthalene)propanal, the enantioselective hydroformylation is preferably carried out at 25° C. under 500 p.s.i. pressure of a 1:1 mixture of H$_2$ and CO. A mixture of 6-methoxy-2-vinylnapthalene and the chiral rhodium complex in a non-polar organic solvent such as benzene, hexane, or triethylsilane is shaken at room temperature for 18 h. In this preferred embodiment a molar ratio between 0.0025:1 to 0.05:1 of rhodium catalyst to vinyl compound is preferred. A molar ratio between 1:1 to 1:1.2 of metal to organophosphorus ligand is preferred.

Using these preferred conditions an ee between 35–72% of the S enantiomer of 2-(2-naphthyl)propanal and a yield between 75–95% will generally be obtained. Isolation of the product aldehyde can be achieved by flash column chromatography of the reaction mixture on silica gel using 10% diethyl ether/hexane as eluent.

General Procedures for the Preparation of Chiral, O-Substituted Carbohydrate Phosphinite and Phosphite Ligands

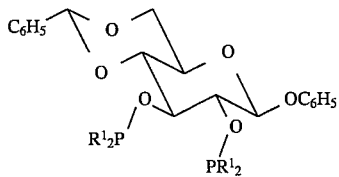

Ligand 1; R$^1$=3,5-(CF$_3$)$_2$C$_6$H$_3$
Ligand 2; R$^1$=Ph (phenyl)
Ligand 3; R$^1$=4-FC$_6$H$_4$
Ligand 4; R$^1$=(4-CF$_3$)C$_6$H$_4$ The ligands 1 through 4 above were prepared according to the method previously reported in U.S. Pat. No. 5,175,335, which is hereby generally incorporated by reference. However, a modified procedure for the synthesis of Ar$_2$PCl (ligand 5) was developed (see below). All reactions were carried out under a N$_2$ atmosphere using standard Schlenk techniques or a Vacuum Atmospheres Co. Drybox. Solvents were distilled and degassed prior to use.

Example of Modified Procedure for Synthesis of Ligand 5, Ar$_2$PCl Species; Di-[(3,5-bis-trifluoro-)methyl)phenyl]chlorophosphine A 1.0M solution of (3,5-bis-trifluoromethyl)phenylmagnesium bromide was prepared in the dry box by slow addition of 18.5 g (60 mmol) of (3,5-bis-trifluoromethyl-)bromobenzene in 40 mL of THF to a slurry of Mg turnings in 20 mL of THF. After 1 h, this solution was added slowly to a solution of 5.0 g (29 mmol) of $Et_2NPCl_2$ in 30 mL of THF at 0° C. After 2 h, the mixture was concentrated in vacuo. Cyclohexane (100 mL) was added and the mixture was filtered to provide a solution of [di-3, 5-bis(trifluoromethyl)-phenyl](diethylamino)phosphine. Dry HCl was passed through this solution for 1 h. After filtration and concentration, 12.4 g (88%) of di-[(3,5-bis-trifluoromethyl)-phenyl]chlorophosphine was collected as a white solid. $^{31}P$ ($C_6D_6$) δ70.4, s. $^1H$ ($C_6D_6$) δ7.54 (s, 1) 7.66 (d, 1, J=7 Hz).

SYNTHESIS OF CATALYSTS

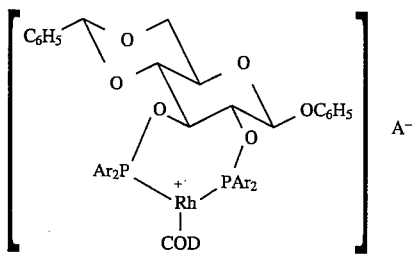

Catalyst 1: Ar=3,5-$(CF_3)_2C_6H_3$; A=$BF_4$ (Phenyl
2,3-bis-O-{[di-(3,5-bis-trifluoro-methyl)phenyl]phosphino}-4,6-benzylidene-β-D-glucopyranoside)-(1,5-cyclooctadienyl) Rhodium(I) Tetrafluoroborate To a solution of 89 mg (0.22 mmol) of $(COD)_2RhBF_4$ in 2 mL of $CH_2Cl_2$ was added a solution of 300 mg (0.24 mmol) of ligand 1 in 2 mL of $CH_2Cl_2$. After 30 min, the mixture was concentrated to give a 2:1 mixture of complexes of catalyst 1. Major complex showed: $^{31}P$ NMR δ126.7 (dd, 1, J=40, 184 Hz), 123.0 (dd, 1, J=40, 179 Hz); Minor complex showed: $^{31}P$ NMR δ139.7 (dd, 1, J=48, 234 Hz), 124.1 (dd, 1, J=48, 240 Hz).

Catalyst 2: Ar=Ph; A=$BF_4$ (Phenyl
2,3-bis-O-diphenylphosphino)-4,6-benzylidene-β-D-glucopyranoside)-(1,5-cyclooctadienyl) Rhodium(I) Tetrafluoroborate In a similar fashion, catalyst 2 was prepared from 31 mg of $(COD)_2RhBF_4$ and 57 mg of ligand 1. Catalyst 2 showed: $^{31}P$ NMR δ134.5 (dd, 1, J=28, 179 Hz), 137.5 (dd, 1, J=28, 178 Hz).

Catalyst 3: Ar=3,5-$(CF_3)_2C_6H_3$; A=$OSO_2CF_3$ (Phenyl
2,3-bis-O-{[di-(3,5-bis-trifluoro-methyl)phenyl]phosphino}-4,6-benzylidene-β-D-glucopyranoside)-1,5-cyclooctadienyl)rhodium (I) Trifluoromethanesulfonate In a similar fashion, catalyst 3 was prepared from 40 mg of $(COD)_2Rh(OSO_2CF_3)$ and 100 mg of ligand 1. Catalyst 3 showed: $^{31}P$ NMR δ122.6 (dd, 1, J=44, 176 Hz), 126.0 (dd, 1, J=44, 166 Hz).

Catalyst 4: Ar=4-$FC_6H_4$; A=$BF_4$ (Phenyl
{2,3-bis-O-[di-(4-fluorphenyl)-phosphino]}-4,6-benzylidene-β-D-glucopyranoside)
(1,5-Cyclooctadienyl)rhodium (I) Tetrafluoroborate In a similar fashion, catalyst 4 was prepared from 49 mg (0.121 mmol) of $(COD)_2RhBF_4$ and 100 mg (0.128 mmol) of 3. Catalyst 4 showed: $^{31}P$ ($CDCl_3$) δ131.3 (dd, 1, J=30, 181), 136.0 (dd, 1, J=32, 179 Hz).

Catalyst 5: Ar=3,5-$(CF_3)_2C_6H_3$; A=$SbF_6$ (Phenyl
(2,3-bis-O-{[di-(3,5-bis-trifluoro-methyl)phenyl]phosphino}-4,6-benzylidene-β-D-glucopyranoside)-(1,5-cyclooctadienyl) Rhodium (I) Hexafluoroantiomanate In a similar fashion, catalyst 5 was prepared from 42 mg (0.076 mmol) of $(COD)_2RhSbF_6$ and 100 mg (0.080 mmol) of ligand 1. A ca. 4:1 mixture of complexes of catalyst 5 was obtained. Major complex showed: $^{31}P$ NMR δ0.126.6 (dd, 1 J=34, 182 Hz), 130.7 (dd, 1, J=34, 186 Hz); Minor complex showed: $^{31}P$ NMR δ125.6 (dd, 1, J=44, 239 Hz), 139.8 (dd, 1, J=44, 236 Hz).

Catalyst 6: Ar=(4-$CF_3$)$C_6H_4$; A=$BF_4$ (Phenyl
(2,3-bis-O-{[di-(4-trifluoromethyl)-phenyl]phosphino}-4,6-benzylidene-β-D-glucopyranoside)-(1,5-cyclooctadienyl) Rhodium (I) Tetrafluoroborate A solution of catalyst 6 was prepared in situ from ligand 4 and $(COD)_2RhBF_4$.

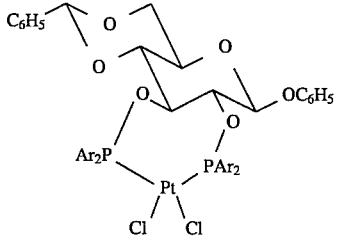

Catalyst 7: Ar=Ph

{(Phenyl
[2,3-bis-O-(diphenylphosphino)]-4,6-benzylidene-β-D-glucopyranoside}platinum (II) Dichloride To a solution of 50 mg (0.11 mmol) of $(PhCN)_2PtCl_2$ in 3 mL of benzene was added a solution of 90 mg (0.13 mmol) of ligand 2 in 2 mL of benzene. After 1 h, the mixture was filtered through a glass wool plug and concentrated to give catalyst 7: $^{31}P$ NMR δ95.1 (d, 1, J=11 Hz), 94.4 (d, 1, J=11 Hz).

Catalyst 8: Ar=3,5-($CF_3$)$_2C_6H_3$

{(Phenyl
{[di-(3,5-bis-trifluoromethyl)-phenyl]phosphino}-4,6-
benzylidene-β-D-glucopyranoside}platinum (II)
Dichloride A solution of catalyst 8 was prepared in situ from ligand 1 and $(PhCN)_2PtCl_2$.

Catalyst 9: Chiral Iridium Catalyst

Preparation of Chiral Iridium Catalyst

To a solution of 50 mg (0.074 mmol) of $[Ir(COD)Cl]_2$ in 5 mL of $CH_3CN$ was a added a solution of 198 mg (0.158 mmol) of ligand 1 in 5 mL of $CH_3CN$. After 1 h, the solution was concentrated to give catalyst 9 as a yellow-orange powder.

Catalyst 10: Chiral Cobalt Catalyst

Chiral cobalt catalyst 10 was generated in situ from 4 mg of $Co_2(CO)_8$ and 22 mg of ligand 1 in 2 mL of THF.

EXAMPLES 1–36

General Methods for Enantioselective Hydroformylation of Vinyl Compounds, for Examples 1–36

Results and reaction conditions for the enantioselective hydroformylation of vinyl compounds are shown in Tables I–IV. With a few exceptions which are noted, the hydroformylations were conducted by shaking a solution of the vinyl compound under a pressure of $H_2$ and CO at the noted temperature. Conversions were determined by integration of the formyl protons of the product aldehydes and the vinyl protons of the vinyl compounds in the $^1$H NMR spectrum of the crude product mixture. EE's were determined after reduction of the crude mixture with lithium aluminum hydride to generate the corresponding primary alcohols by HPLC using a Bakerbond Chiral DNBPG Chiralcel OJ or OB column (J. T. Baker, Phillipsburg, N.J.): 2–5% i-PrOH/Hexane, 1 mL/min., 40° C. HPLC samples were passed through a short pad of silica gel and eluted with a hexane/$Et_2O$ gradient prior to analysis. In some instances ee's were determined by $^1$H NMR using chiral shift reagent $Eu(hfc)_3$ or by gas chromatographic separation using a Chiraldex G-TA capillary column (Aztec, Whippany, N.J.). EE values refer to an excess of the S-enantiomer. Enriched samples of the S-alcohols from the hydroformylation of 2-vinylnapthalene and 6-methoxy-2-vinylnapthalene were obtained by diisobutylaluminum hydride reduction of the corresponding nitrile [*J. Am. Chem. Soc.* 114, 6265 (1992)] followed by lithium aluminum hydride reduction. The relative assignments of the other hydroformylation products were assigned by analogy to be enriched with the S-enantiomer.

Typical Procedure for Hydroformylation Reactions

In the dry box a 140 mL glass liner was charged with 2.0 mmol of vinyl compound, 0.003 mmol of catalyst/cocatalyst, and 10 mL of solvent. This liner was placed in a shaker tube and pressurized with a 1:1 mixture of hydrogen and carbon monoxide. After venting, the mixture was pressurized with the hydrogen, carbon monoxide mixture and shaken at the given temperature. Upon completion, the mixture was vented and the glass liner was removed from the shaker tube. The solution was filtered through celite and concentrated. Percent conversions were determined by $^1$H NMR integration of the resonances corresponding to the starting vinyl compound and product aldehydes. The branched aldehyde to linear aldehyde ratio (b/l) was determined by $^1$H NMR integration of the resonances corresponding to the aldehyde protons or by GC.

The crude mixture was dissolved in 10 mL of ether and 50 mg (1.3 mmol) of $LiAlH_4$ was added. After 3 h, water (4 drops), 15% NaOH (4 drops) and water (12 drops) was added carefully. After 30 min. $Na_2SO_4$ was added and the mixture was filtered and concentrated. Flash chromatography on silica gel using 40% ether/hexane as eluant gave 2-substituted-1-propanols. The ees of these alcohols were determined by analysis on either an OB or OJ chiralcel HPLC column using an i-propanol/hexane mixture as eluant.

EXAMPLES 1–12

TABLES I AND II

Hydroformylation of 2-Vinylnapthalene Using Catalyst Composition 1 or 2

Example 1

Following the general procedure, a mixture of 300 mg (2.0 mmol) of 2-vinylnapthalene and 5 mg of catalyst 1 in 10 mL of $Et_3SiH$ was pressurized at room temperature to 1600 psi using the $H_2$/CO mixture. After 18 h, the mixture was manipulated as described: conversion=20%; b/l=22; ee=72%.

Example 2

The reaction was carried out similar to Example 1, using hexane as solvent and 500 psi of $H_2$/CO provided the following: conversion=100%; b/l=20; ee=50%.

Example 3

The reaction was carried out similar to Example 1, using hexane and triethylformate as solvent and 1600 psi of $H_2$/CO provided the following: conversion=85%; b/l=20; ee=17%. In this case the ee was determined on the diethyl acetal resulting from in situ trapping of 2-(2-napthyl)-1-propanal.

Examples 4–9 were performed in a similar fashion under the conditions described in Table I.

Examples 10–12 were performed in a similar manner using catalyst 2 under the conditions described in Table II.

TABLE I

Asymmetric Hydroformylation of 2-Vinylnaphthalene Using Catalyst 1

| Ex. | Solvent | Pressure (psi) | Temp. (°C.) | b/l | Conv. (%) | ee (%) |
|---|---|---|---|---|---|---|
| 1 | $Et_3SiH$ | 1600 | ambient | 22 | 20 | 72 |
| 2 | Hexane | 500 | ambient | 20 | 100 | 49 |
| 3 | Hexane + $CH(OEt)_3$ | 1600 | ambient | 20 | 85 | 17 |
| 4 | Hexane | 1600 | ambient | 26 | 53 | 51 |
| 5 | Hexane | 2400 | ambient | 24 | 80 | 31 |
| 6 | Benzene | 1600 | ambient | 33 | 43 | 38 |
| 7 | THF | 1600 | ambient | 40 | 71 | 12 |
| 8 | THF | 1600 | 70 | 11 | 100 | 10 |
| 9 | THF | 2400 | ambient | — | 100 | 7 |

TABLE II

Asymmetric Hydroformylation of 2-Vinylnaphthalene Using Catalyst 2

| Ex. | Solvent | Pressure (psi) | Temp. (°C.) | b/l | Conv. (%) | ee (%) |
|---|---|---|---|---|---|---|
| 10 | Benzene | 1600 | ambient | 21 | 18 | 10 |
| 11 | Benzene | 1600 | 70 | 12 | 100 | 1 |
| 12 | THF | 1600 | 70 | 10 | 100 | 11 |

EXAMPLES 13–26

TABLE III

Examples 13–26 were performed in a similar fashion using the appropriate vinyl compound and catalyst as indicated. Abbreviations are as follows 6-methoxy-2-vinylnapthalene (MVN), styrene (ST), 4-isobutylstyrene (IBS), 4-methylstyrene (4-MeST), vinyl acetate (VA).

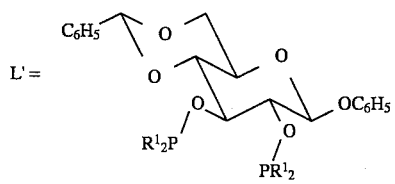

TABLE III

Other Asymmetric Hydroformylation Reactions Using L'Rh(COD)A Complexes

| Ex. | Substrate | $R^1$ | A | Solvent | b/l | Conv. (%) | ee (%) |
|---|---|---|---|---|---|---|---|
| 13 | VN | $(4\text{-}CF_3)C_6H_4$ | $BF_4$ | Hexane | 10 | 40 | 10 |
| 14 | MVN | $(4\text{-}CF_3)C_6H_4$ | $BF_4$ | Hexane | 8 | 10 | 15 |
| 15 | MVN | $4\text{-}FC_6H_4$ | $BF_4$ | Hexane | 7 | 10 | 5 |
| 16 | VN | $3,5\text{-}(CF_3)_2C_6H_3$ | $SbF_6$ | Hexane | 18 | 100 | 19 |
| 17 | ST | $3,5\text{-}(CF_3)_2C_6H_3$ | $BF_4$ | Hexane | 29 | 50 | 24 |
| 18 | ST | $3,5\text{-}(CF_3)_2C_6H_3$ | $SbF_6$ | Hexane | 19 | 63 | 17 |
| 19 | ST | $3,5\text{-}(CF_3)_2C_6H_3$ | $OT_f$ | Hexane | 21 | 53 | 14 |
| 20 | 4-MeST | $3,5\text{-}(CF_3)_2C_6H_3$ | $BF_4$ | Hexane | 16 | 43 | 30 |
| 21 | IBS | $3,5\text{-}(CF_3)_2C_6H_3$ | $BF_4$ | $Et_3SiH$ | 16 | 1 | 43 |
| 22 | MVN | $3,5\text{-}(CF_3)_2C_6H_3$ | $BF_4$ | Hexane | 15 | 60 | 44 |
| 23 | MVN | $3,5\text{-}(CF_3)_2C_6H_3$ | $BF_4$ | $Et_3SiH$ | 20 | 5 | 70 |
| 24 | MVN | $3,5\text{-}(CF_3)_2C_6H_3$ | $BF_4$ | $i\text{-}Pr_3SiH$ | 14 | 14 | 16 |
| 25 | VA | $3,5\text{-}(CF_3)_2C_6H_3$ | $BF_4$ | Hexane | 12 | 10 | 14 |
| 26 | VA | $3,5\text{-}(CF_3)_2C_6H_3$ | OTf | Hexane | 9 | 10 | 11 |

EXAMPLES 27–30

Asymmetric Hydroformylation of 6-Methoxy-2-vinylnapthalene and 2-Vinylnapthalene Using Chiral Platinum Catalysts

Example 27

Following the general procedure, a mixture of 400 mg (2.2 mmol) of 6-methoxy-2-vinylnapthalene, 3 mg (0.016 mmol) of $SnCl_2$, 2 mg (0.016 mmol) of 4-methoxyphenol and 10 mg (0.001 mmol) of {(phenyl [2,3-bis-O-(diphenylphosphino)]-4,6-benzylidene-β-D-glucopyranoside}platinum (II) dichloride (catalyst 7) in 10 mL of benzene was pressurized at ambient temperature to 2400 psi using the $H_2/CO$ mixture. After 44 h, the mixture was manipulated as described: conversion=100%; b/l=0.7; ee=9%.

Example 28

The reaction was carried out similar to Example 31, except performing the reaction at 60° C. which provided the following: conversion=100%; b/l=1.3; ee=9%.

Example 29

The reaction was carried out similar to Example 31, using benzene and triethylformate as solvent, which provided the following: % conversion=80%; b/l=1.5; ee=9%. In this case the ee was determined on the diethyl acetal resulting from in situ trapping of 2-(2-napthyl)-1-propanal.

Example 30

In this case a benzene solution of chiral platinum catalyst, (phenyl 2,3-bis-O-{[di-(3,5-bis-trifluoromethyl)-phenyl]phosphino}-4,6-benzylidene-β-D-glucopyranoside)platinum(II) dichloride (catalyst 8), was generated from 24 mg (0.02 mmol) of 1 and 7 mg (0.02 mmol) of dichlorobis(benzonitrile)platinum (II). This catalyst solution, 300 mg (2.0 mmol) of 2-vinylnapthalene, 6 mg (0.032 mmol) of $SnCl_2$, 2 mg (0.016 mmol) of 4-methoxyphenol, and 8 mL of benzene was placed in a glass liner. The reaction was performed at 60° C. and 2400 psi pressure of $H_2/CO$ for 18 h to provide the following: conversion=90%; b/l=2.7; ee=5%.

EXAMPLE 31

Asymmetric Hydroformylation of 6-Methoxy-2-vinylnapthalene Using Chiral Iridium Catalysts The reaction was performed in a similar manner to the rhodium-catalyzed hydroformylations; 300 mg of MVN, 5 mg of chiral iridium catalyst 9, and 10 mL of THF. This experiment was conducted at 80° C. using 3000 psi of $H_2/CO$ to provide the following: conversion 37%; b/l=10; ee=30%.

EXAMPLE 32

Asymmetric Hydroformylation of 6-Methoxy-2-vinylnapthalene Using Chiral Cobalt Catalysts This reaction was performed in a similar manner to the rhodium-catalyzed hydroformylations, except the chiral cobalt catalyst 10 was generated in situ from 4 mg of $Co_2(CO)_8$ and 22 mg of 5 in 2 mL of THF. The reaction was performed using this catalyst solution, 300 mg of MVN, and 8 mL of THF. The reaction was conducted at 120° C. and 5000 psi of $H_2/CO$ to provide the following: conversion= 10%; b/l=3; ee=1%.

What is claimed is:

1. A catalyst composition comprising one or more metals selected from the group consisting of Co, Rh, Ir and Pt, and a chiral nonracemic ligand of formula II $$(R^1)_2\text{—P—O—}R^2\text{—O—P—}(R^1)_2 \qquad \text{II}$$

wherein each $R^1$ is an electron-withdrawing group selected from the group consisting of an aromatic hydrocarbyl substituted with one or more halo, halogen-substituted alkyl groups, cyano, alkylsulfonyl, carboalkoxy, quaternary ammonium, nitro, amido or keto groups and a heteroaromatic optionally substituted with one or more halo, halogen-substituted alkyl groups, cyano, alkylsulfonyl, carboalkoxy, quaternary ammonium, nitro, amido or keto groups; and $R^2$ is a $C_4$ to $C_{40}$ dideoxy carbohydrate; optionally substituted with one or more hydrocarbyl, halo, alkoxy, carboalkoxy, hydroxy, amido or keto groups.

2. The composition of claim 1, wherein the metal is Rh.

3. The composition of claim 1, wherein the ratio of ligand to metal is from about 1 to 1, to about 1.2 to 1.

4. The composition of claim 1, wherein $R^1$ is 3,5-$(CF_3)_2C_6H_3$.

5. The composition of claim 1, wherein $R^2$ is 4,6-benzylidene-β-D-glycopyranoside.

6. The composition of claim 1, wherein the metal is Rh and the ligand of formula II is phenyl 2,3-bis-O-{[di-(3,5-bis-trifluoromethyl)-phenyl]phosphino}-4,6-benzylidene-β-D-glucopyranoside.

* * * * *